US00PP09722P

United States Patent [19]

Ilsink

[11] Patent Number: Plant 9,722

[45] Date of Patent: Dec. 3, 1996

[54] FLORIBUNDA VARIETY NAMED 'INTERLIS'

[75] Inventor: G. P. Ilsink, Doorn, Netherlands

[73] Assignee: DeVor Nurseries, Inc., Watsonville, Calif.

[21] Appl. No.: 597,900

[22] Filed: Feb. 7, 1996

[51] Int. Cl.[6] ..... A01H 5/00

[52] U.S. Cl. ..... Plt./26

[58] Field of Search ..... Plt./26, 25, 23

*Primary Examiner*—Howard J. Locker

*Attorney, Agent, or Firm*—Christie, Parker & Hale, LLP

[57] ABSTRACT

A new variety of floribunda rose producing light cream pink flowers with a general tonality of pink from a distance.

1 Drawing Sheet

SUMMARY OF THE INVENTION

The present invention relates to a new and distinct variety of rose of the floribunda rose class which was originated by my crossing as seed parents two unnamed, unpatented, proprietary seedlings of my creation. The varietal denomination of this new rose is 'Interlis'.

Among the novel characteristics possessed by this new variety which distinguishes it from its parents are its ability to produce commercially desirable sprays of attractive flowers for the cut flower market. Plants of the new variety are able to produce about 140 to 160 sprays per square meter per year in a greenhouse. The sprays have stem lengths of as much as 60 cm or more and a vase life of about 10 to 12 days.

Asexual reproduction by budding of the new variety as performed in Watsonville, Calif., shows that the foregoing and other distinguishing characteristics come true to form and are established and transmitted through succeeding propagations.

BRIEF DESCRIPTION OF ILLUSTRATION

The accompanying illustration shows typical specimens of the flowers and vegetative growth of the new variety depicted in color as nearly true as it is reasonably possible to make the same in a color illustration of this character. Phenotypic expression, including colors, may vary depending upon growing conditions, such as climate, soil, and environmental conditions.

DESCRIPTION OF THE NEW VARIETY

The following is a detailed description of my new variety, with color terminology in accordance with The Royal Horticultural Society Colour Chart (R.H.S.C.C.). The terminology used in color description herein refers to plate numbers in the aforementioned color chart. Where general terms such as average, normal, ordinary, medium, etc. are used, the characteristics so described are not considered distinguishing.

Parentage: Seedling.

*Seed parent.*—Unnamed seedling.

*Pollen parent.*—Unnamed seedling.

Class Floribunda.

The following information is from observations made of specimens grown outdoors in Watsonville, Calif. in the month of April.

FLOWER

Blooming habit: Recurrent.

A. Bud:

(1) *Size.*—Large.

(2) *Form.*—Small, about 1.5 to 2 cm long by about 1.5 cm wide; ovoid.

(3) *Color.*—As sepals divide, bud color is near 50B.

(4) *Sepals.*—About 2 cm, pointed ends with small leaf-like projections from sides. Color: Near 146C with a tinge of near 179A.

(5) *Peduncle.*—Length: About 7.5 to 12 cm. Strength: Sturdy, erect, slender. Color: Near 144A tinged with near 184C.

(6) *Bracts.*—2 to 3 per bud. Color — near 137A. Form — leaf-shaped when mature, broadly lanceolate with caudate apex when young. Location in relation to flower — about 2.5 cm below calyx.

B. Bloom:

(1) *Size.*—About 4.5 cm.

(2) *Borne.*—Singly and in sprays of to 2 to 11 blooms.

(3) *Form.*—Imbricated, high centered at first, becoming informal at maturity, petals reflex at maturity.

(4) *Petalage.*—Number of petals under normal conditions — about 35 to 43.

(5) *Color: (⅓ to ½ open).*—Outer petals — Top surface near 36B, ⅛ of base near 158C. — Undersurface near 37D, ⅛ of base near 158C. Inner petals — Top surface near 36B, ⅛ of base near 158C. Inner petals — Undersurface near 37D, ⅛ of base near 158C. Base of petals — Near 2D. General tonality from a distance — pink.

(6) *Color: (fully open).*—Outer petals — Top surface near 49C, ¼ of base near 158C. — Undersurface near 50D. ¼ of base near 158C. Inner petals — Top surface near 36C, ¼ of base near 158C. — Undersurface near 50D, ¼ of base near 158C. Base of petals — Near 160C. General tonality from a distance — pink.

(7) *Color change.*—Blooms lightens to a softer pink. Petal top surface — Lightens to a softer pink. Petal undersurface — Lightens to a softer pink. General tonality from a distance — pink.

C. Petals:

(1) *Texture.*—Thick, smooth.

(2) *Appearance.*—Very slight velvety finish on both sides.

(3) *Form.*—Elliptic with very slight ruffling at edges.

(4) *Arrangement.*—Imbricated.

(5) *Petaloids in center.*—Many.

(6) *Persistence.*—Petals drop off cleanly.

(7) *Fragrance.*—Very slight musk fragrance.

(8) *Lasting quality.*—About 10 to 12 days in vase after cutting.

REPRODUCTIVE ORGANS

A. Stamens, filaments and anthers:
*Arrangement.*—Introrse, regularly arranged around styles.
*Filaments.*—Color near 145C.
*Anthers.*—color near 20C.
*Pollen.*—Color near 20C.

B. Styles: Bunched, even, medium length.
*Stigma.*—Color — near 160D.

PLANT

A. Form: Upright, free branching.
B. Growth: Vigorous.
C. Foliage: Compound 3 to 7 leaflets.
(1) *Size.*—Small.
(2) *Quantity.*—Abundant.
(3) *Color.*—New foliage: Upper side near 137A edged with near 184A. Underside near 146B edged with near 184A Old foliage: Upper side near 147A. Underside — near 147B.
(4) *Shape.*—Ovate.
(5) *Texture.*—Upper side is smooth, leathery and underside is smooth and slightly leathery.
(6) *Edge.*—Serrated.
(7) *Serration.*—Denticulate.
(8) *Petiole color.*—Top surface — near 146A. Underside near 146B.
(9) *Stipules.*—Adnate, medium, slightly bearded, parallel.
(10) *Auricle.*—Facing forward thin, slightly glandular.
(11) *Rachis.*—Smooth underneath.
(12) *Resistance to disease.*—Very resistant to mildew, rust and blackspot.

D. Wood
(1) *New wood.*—Color — New shoots near 146B. Bark — smooth.
(2) *Old wood.*—color — near 146A. Bark — smooth.
(3) *Flower stem length from last cutting.*—About 50 cm to about 60 cm.

E. Thorns:
*Quantity (main stalk).*—None.
*On laterals from stalk.*—none.
*Prickles.*—None.

F. Winter hardiness: Winter hardy in coastal California climate.

I claim:

1. A new and distinct variety of rose plant of the floribunda rose class, substantially as shown and described.

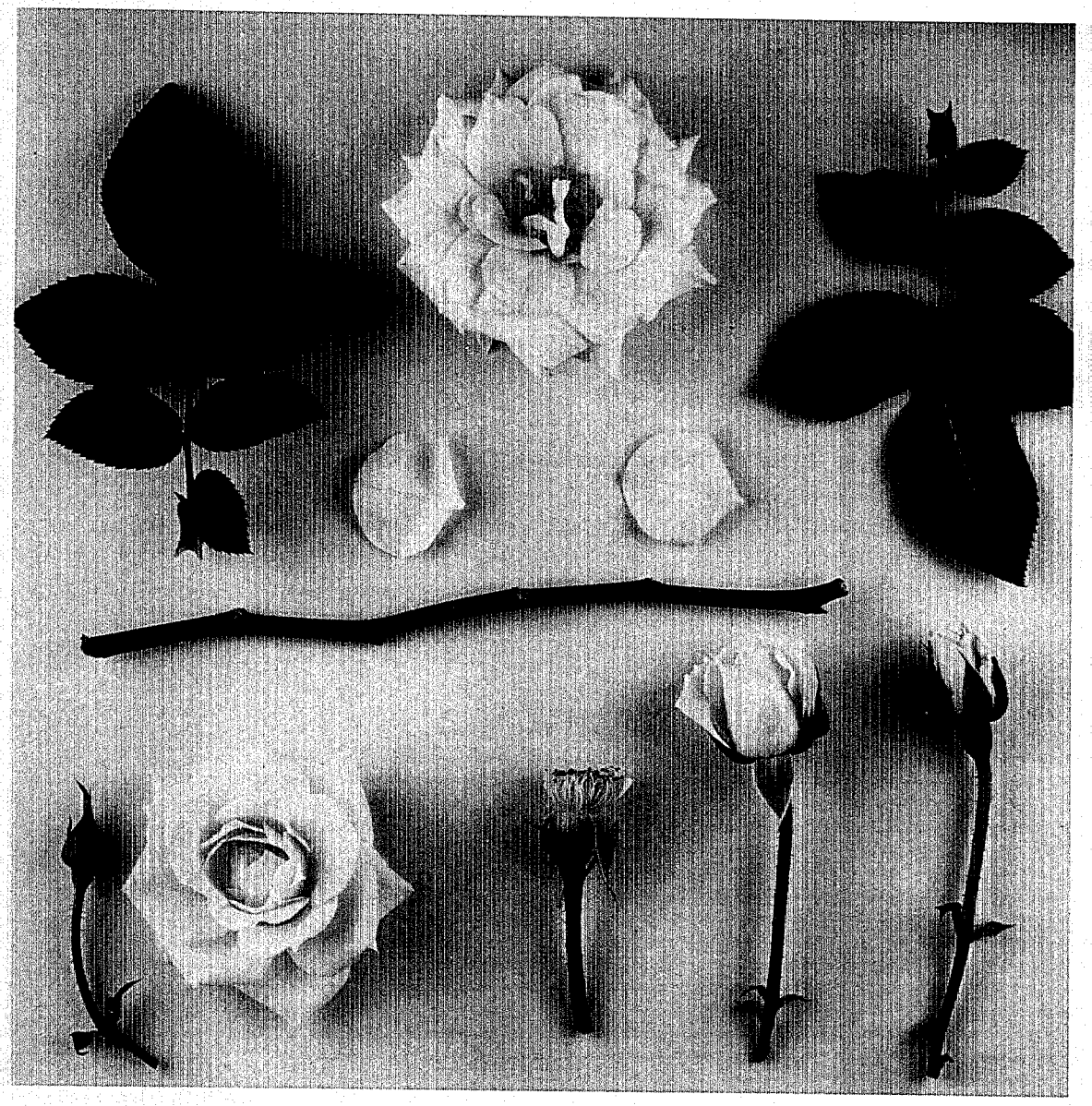

* * * * *